US011109799B2

(12) United States Patent
Ribble et al.

(10) Patent No.: US 11,109,799 B2
(45) Date of Patent: Sep. 7, 2021

(54) MODULAR TURN ASSIST APPARATUS AND METHOD THEREFOR (71) Applicant: Hill-Rom Services, Inc., Batesville, IN (US)

(72) Inventors: David L. Ribble, Batesville, IN (US); Kirsten M. Emmons, Batesville, IN (US); Craig M. Meyerson, Syracuse, NY (US); Thomas F. Heil, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 434 days.

(21) Appl. No.: 16/167,698

(22) Filed: Oct. 23, 2018

(65) Prior Publication Data
US 2019/0117152 A1   Apr. 25, 2019

Related U.S. Application Data (60) Provisional application No. 62/576,275, filed on Oct. 24, 2017.

(51) Int. Cl.
*A61B 5/00* (2006.01)
*A47C 27/08* (2006.01)
(Continued)

(52) U.S. Cl.
CPC ............ *A61B 5/4818* (2013.01); *A47C 27/08* (2013.01); *A61B 5/4809* (2013.01); *A61B 5/6892* (2013.01); *A61G 7/001* (2013.01); *A61G 7/05776* (2013.01); *A47G 2009/003* (2013.01); *A61B 5/024* (2013.01); *A61B 5/0205* (2013.01);
(Continued)

(58) Field of Classification Search
CPC ... A61B 5/4818; A61B 5/6892; A61B 5/4809; A47C 27/08; G08B 21/06; A61G 7/001; A61G 7/008
See application file for complete search history.

(56) References Cited

U.S. PATENT DOCUMENTS 3,284,815 A * 11/1966 Abraham Grossman .................... A61B 6/04
5/607
3,775,785 A * 12/1973 Mittendorf ............... A47G 9/10
5/640

(Continued)

FOREIGN PATENT DOCUMENTS

EP    3015058 A1    5/2016
WO   2004089270 A1   10/2004

OTHER PUBLICATIONS

European Search Report for Application No. 18200545.4, dated Feb. 20, 2019, 7 pages.

*Primary Examiner* — Eric J Kurilla
(74) *Attorney, Agent, or Firm* — Barnes & Thornburg LLP (57) ABSTRACT A therapeutic support apparatus includes a user support surface extending along a longitudinal axis. The user support surface has a head section and a torso section. Each of the head section and the torso section are operable to angle relative to the longitudinal axis. An elevation unit is operable to position at least one of the head section and torso section at angles relative to the longitudinal axis. A monitor acquires data related to a user while sleeping on the user support surface. An alarm is operable to activate based on the data acquired by the monitor.

26 Claims, 7 Drawing Sheets (51) Int. Cl.

| | | |
|---|---|---|
| *G08B 21/06* | (2006.01) | |
| *A61G 7/00* | (2006.01) | |
| *A61G 7/057* | (2006.01) | |
| *A61B 5/11* | (2006.01) | |
| *A47G 9/00* | (2006.01) | |
| *A61B 5/0205* | (2006.01) | |
| *A61B 5/024* | (2006.01) | |
| *A61B 5/08* | (2006.01) | |
| *A61G 7/015* | (2006.01) | |
| *A61G 7/008* | (2006.01) | |
| *A61B 5/318* | (2021.01) | |
| *A61B 5/369* | (2021.01) | |

(52) U.S. Cl.
CPC ............... *A61B 5/0816* (2013.01); *A61B 5/11* (2013.01); *A61B 5/318* (2021.01); *A61B 5/369* (2021.01); *A61B 5/4815* (2013.01); *A61B 2562/0219* (2013.01); *A61G 7/008* (2013.01); *A61G 7/015* (2013.01); *A61G 7/057* (2013.01); *A61M 2230/10* (2013.01); *G08B 21/06* (2013.01)

(56) References Cited

U.S. PATENT DOCUMENTS

| | | | |
|---|---|---|---|
| 4,745,647 A | 5/1988 | Goodwin | |
| 4,841,221 A * | 6/1989 | Barney | G01D 5/14 315/194 |
| 4,962,552 A | 10/1990 | Hasty | |
| 5,103,519 A | 4/1992 | Hasty | |
| 5,138,729 A | 8/1992 | Ferrand | |
| 5,181,288 A | 1/1993 | Heaton et al. | |
| 5,313,679 A * | 5/1994 | Yamaguchi | A47C 19/045 254/93 HP |
| 5,323,500 A | 6/1994 | Roe et al. | |
| 5,345,629 A | 9/1994 | Ferrand | |
| 5,526,543 A | 6/1996 | DiMatteo | |
| 5,664,270 A | 9/1997 | Bell et al. | |
| 5,781,949 A | 7/1998 | Weismiller et al. | |
| 5,802,646 A | 9/1998 | Stolpmann et al. | |
| 5,815,865 A | 10/1998 | Washburn et al. | |
| 5,934,280 A | 8/1999 | Viard et al. | |
| 5,944,066 A | 8/1999 | Viard | |
| 5,966,763 A | 10/1999 | Thomas et al. | |
| 6,212,718 B1 | 4/2001 | Stolpmann et al. | |
| 6,243,894 B1 | 6/2001 | Kosumsuppamala et al. | |
| 6,298,511 B1 * | 10/2001 | Collymore | A61G 7/001 5/615 |
| 6,499,167 B1 * | 12/2002 | Ellis | A61G 7/00 5/709 |
| 6,568,013 B2 | 5/2003 | Perez et al. | |
| 6,584,628 B1 | 7/2003 | Kummer et al. | |
| 6,622,324 B2 | 9/2003 | VanSteenburg et al. | |
| 6,701,558 B2 | 3/2004 | VanSteenburg | |
| 6,735,500 B2 | 5/2004 | Nicholas et al. | |
| 6,839,929 B2 | 1/2005 | Stolpmann | |
| 6,855,158 B2 | 2/2005 | Stolpmann | |
| 6,892,405 B1 | 5/2005 | Dimitriu et al. | |
| 6,904,631 B2 | 6/2005 | Vrzalik et al. | |
| 7,007,330 B2 | 3/2006 | Kuiper et al. | |
| 7,296,312 B2 | 11/2007 | Menkedick et al. | |
| 7,308,725 B2 | 12/2007 | Cazzini et al. | |
| 7,346,945 B2 | 3/2008 | Phillips et al. | |
| 7,346,951 B1 * | 3/2008 | Heaton | A61G 7/008 5/615 |
| 9,241,581 B2 * | 1/2016 | O'Nion | A47D 5/006 |
| D779,236 S * | 2/2017 | Ribble | A61G 7/018 D6/605 |
| 10,426,277 B2 * | 10/2019 | Cerri, III | A47D 15/00 |
| 2003/0226206 A1 * | 12/2003 | Ben-Levi | A61G 7/001 5/615 |
| 2005/0166328 A1 * | 8/2005 | Ben-Levi | A61G 7/001 5/715 |
| 2006/0112489 A1 | 6/2006 | Bobey et al. | |
| 2006/0123552 A1 * | 6/2006 | Ben-Levi | A61G 7/001 5/715 |
| 2007/0143928 A1 | 6/2007 | Biggie et al. | |
| 2007/0163052 A1 | 7/2007 | Romano et al. | |
| 2008/0028533 A1 | 2/2008 | Stacy et al. | |
| 2008/0040860 A1 | 2/2008 | Price et al. | |
| 2008/0263763 A1 * | 10/2008 | Butler | A61G 7/057 5/81.1 R |
| 2009/0106893 A1 * | 4/2009 | Blevins | A61G 7/001 5/81.1 RP |
| 2009/0106906 A1 | 4/2009 | Soltani et al. | |
| 2010/0138998 A1 * | 6/2010 | Wilkinson | A61G 7/001 5/615 |
| 2011/0068928 A1 | 3/2011 | Riley et al. | |
| 2012/0089419 A1 | 4/2012 | Huster et al. | |
| 2012/0312196 A1 | 12/2012 | Newkirk | |
| 2013/0219622 A1 | 8/2013 | Hornbach et al. | |
| 2014/0007353 A1 * | 1/2014 | Stryker | A61G 7/057 5/715 |
| 2014/0047644 A1 | 2/2014 | Mossbeck | |
| 2014/0062342 A1 | 3/2014 | Murphy | |
| 2014/0245539 A1 * | 9/2014 | Ooba | A61G 7/008 5/636 |
| 2014/0259410 A1 | 9/2014 | Zerhusen et al. | |
| 2014/0292529 A1 | 10/2014 | Zerhusen | |
| 2014/0323816 A1 | 10/2014 | Soderberg et al. | |
| 2014/0345060 A1 | 11/2014 | Ribble et al. | |
| 2014/0375451 A1 | 12/2014 | Douglas et al. | |
| 2015/0136146 A1 * | 5/2015 | Hood | A61G 7/0525 128/845 |
| 2015/0164409 A1 * | 6/2015 | Benson | A61B 7/003 600/301 |
| 2015/0335507 A1 * | 11/2015 | Emmons | A61B 5/6892 5/615 |
| 2016/0120716 A1 * | 5/2016 | Ribble | A61B 5/4809 5/616 |
| 2017/0245656 A1 * | 8/2017 | Ribble | A61G 7/001 |
| 2017/0333270 A1 * | 11/2017 | Peng | A61G 7/001 |
| 2019/0209405 A1 * | 7/2019 | Sayadi | A61B 5/4809 |
| 2019/0231624 A1 * | 8/2019 | Lafleche | A61G 7/1021 |
| 2020/0100969 A1 * | 4/2020 | Ribble | A61G 7/0508 |

* cited by examiner

MODULAR TURN ASSIST APPARATUS AND METHOD THEREFOR

CROSS-REFERENCE TO RELATED APPLICATIONS

This application claims priority under 35 U.S.C. § 119(e) to U.S. Provisional Application No. 62/576,275, filed Oct. 24, 2017, which is expressly incorporated by reference herein.

BACKGROUND

The present disclosure relates to a therapeutic support apparatus. More specifically, the present disclosure relates to a therapeutic support apparatus with sleep state monitoring.

The subject matter disclosed herein relates generally to adverse event mitigation devices, systems, and methods and, more particularly, but not exclusively, to devices, systems, and methods for the prevention and treatment of sleep apnea. These devices, systems, and methods may include an active intervention, a passive intervention, or a continuous intervention. The embodiments described herein may also be effective in reducing snoring.

While various adverse event mitigation devices, systems, and methods have been developed, there is still room for improvement. Thus, a need persists for further contributions in this area of technology.

SUMMARY

The present disclosure includes one or more of the features recited in the appended claims and/or the following features which, alone or in any combination, may comprise patentable subject matter.

According to one aspect of the embodiments, a therapeutic support apparatus includes a user support surface extending along a longitudinal axis. The user support surface may have a head section and a torso section. Each of the head section and the torso section may be operable to angle relative to the longitudinal axis. An elevation unit may be operable to position at least one of the head section and torso section at angles relative to the longitudinal axis. A monitor may acquire data related to a user while sleeping on the user support surface. An alarm may be operable to activate based on the data acquired by the monitor. At least one of the elevation unit and the alarm may be activated in response to the data acquired by the monitor to control oxygen desaturation of the user.

In some embodiments, the elevation unit may include a first plate couple to a second plate at a hinge. At least one inflatable bladder may be positioned between the first plate and the second plate. The at least one inflatable bladder may be operable to inflate and deflate to move the second plate to an angle relative to the first plate. The at least one inflatable bladder may include a head bladder and a torso bladder. The head bladder may be operable to inflate and deflate to move a head section of the second plate to a head angle relative to the first plate. The torso bladder may be operable to inflate and deflate to move a torso section of the second plate to a torso angle relative to the first plate. The head bladder may be operable to inflate and deflate to a first capacity. The torso bladder may be operable to inflate and deflate to a second capacity. The first capacity may be different than the second capacity. The head bladder and the torso bladder may cooperate to form a compound angle. The head angle and the torso angle may be different. The head angle may be greater than the torso angle. The head section of the second plate and the torso section of the second plate may cooperate to form a compound angle.

Alternatively or in addition to, the elevation unit may change a head angle of the head section of the second plate in response to the data acquired by the monitor. The elevation unit may change the torso angle of the torso section of the second plate in response to the data acquired by the monitor. The elevation unit may move the head section of the second plate in response to the data acquired by the monitor to alter a sleep stage of the user. The elevation unit may move the torso section of the second plate in response to the data acquired by the monitor to alter a sleep stage of the user. At least one tether may couple the first plate and the second plate. The elevation unit may include an expandable envelope. The first plate, the second plate, and the at least one inflatable bladder may be housed within the expandable envelope.

Optionally, the elevation unit may include a first plate couple to a second plate at a first hinge. A third plate may be coupled to the second plate at a second hinge. The first plate, the second plate, and the third plate may be formed from a flexible material. At least one inflatable right bladder may be positioned between the first plate and the second plate. At least one inflatable left bladder may be positioned between the second plate and the third plate. The at least one inflatable right bladder may be operable to inflate and deflate to move the second plate to an angle relative to the first plate. The at least one inflatable left bladder may be operable to inflate and deflate to move the third plate to an angle relative to the second plate. The at least one inflatable right bladder may have a right head bladder and a right torso bladder. The right head bladder may be operable to inflate and deflate to move a head section of the second plate to a head angle relative to the first plate. The right torso bladder may be operable to inflate and deflate to move a torso section of the second plate to a torso angle relative to the first plate. The right head bladder may be operable to inflate and deflate to a first capacity. The right torso bladder may be operable to inflate and deflate to a second capacity, wherein the first capacity is different than the second capacity. The right head bladder and the right torso bladder may cooperate to form a compound angle. The at least one inflatable left bladder may have a left head bladder and a left torso bladder. The left head bladder may be operable to inflate and deflate to move a head section of the second plate to a head angle relative to the first plate. The left torso bladder may be operable to inflate and deflate to move a torso section of the second plate to a torso angle relative to the first plate. The left head bladder may be operable to inflate and deflate to a first capacity. The left torso bladder may be operable to inflate and deflate to a second capacity. The first capacity may be different than the second capacity. The left head bladder and the left torso bladder may cooperate to form a compound angle.

It may be desired that the user support surface is positioned on a frame. The elevation unit may be positioned between the frame and the user support surface. The elevation unit may include at least one strap to secure the elevation unit to the frame. The alarm may be an audible alarm. The alarm may be a visual alarm. The data acquired may include at least one of head angle and torso angle. The data acquired may include at least one of respiratory rate, respiratory amplitude, oxygen saturation, apnea hypopnea index, sleep state, and snoring.

According to another aspect of the embodiments, a method of controlling oxygen desaturation of a user on a therapeutic support apparatus having a head section and a torso section is provided. The head section and the torso may each be operable to angle relative to a longitudinal axis. The method may include positioning the head section of the therapeutic support apparatus at a head angle with an elevation unit. The torso section of the therapeutic support apparatus may be positioned at a torso angle with the elevation unit. Data related to a user while sleeping on the therapeutic support apparatus may be acquired. The method may include activating at least one of the elevation unit or an alarm in response to the data acquired.

In some embodiments, positioning the head section of the therapeutic support apparatus at a head angle may include inflating a head bladder of the elevation unit. Positioning a torso section of the therapeutic support apparatus at a torso angle may include inflating a torso bladder of the elevation unit. Positioning the head section of the therapeutic support apparatus at a head angle may include inflating the head bladder of the elevation unit to a first capacity. Positioning a torso section of the therapeutic support apparatus at a torso angle may include inflating the torso bladder of the elevation unit to a second capacity. The first capacity may be different than the second capacity. The head bladder and the torso bladder may cooperate to form a compound angle. The head section of the therapeutic support apparatus may be positioned at a head angle that is different than the torso angle of the torso section of the therapeutic support apparatus. The head section of the therapeutic support apparatus may be positioned at a head angle that is greater than the torso angle of the torso section of the therapeutic support apparatus. The torso section of the therapeutic support apparatus may be positioned at a torso angle that cooperates with the head angle of the head section of the therapeutic support apparatus to form a compound angle.

Alternatively or in addition to, the head angle of the head section of the therapeutic support apparatus may be altered with the elevation unit in response to the data acquired by the monitor. The torso angle of the torso section of the therapeutic support apparatus may be altered with the elevation unit in response to the data acquired by the monitor. The head section of the therapeutic support apparatus may be moved with the elevation unit in response to the data acquired by the monitor to alter a sleep stage of the user. The torso section of the therapeutic support apparatus with the elevation unit may be moved in response to the data acquired by the monitor to alter a sleep stage of the user.

Optionally, the elevation unit may be positioned between a frame and the user support surface. The elevation unit may be secured to the frame with at least one strap. The method may include activating an audible alarm. The method may include activating a visual alarm. Data may be acquired related to at least one of head angle and torso angle. Data may be acquired related to at least one of respiratory rate, respiratory amplitude, oxygen saturation, apnea hypopnea index, sleep state, and snoring.

According to yet another aspect of the embodiments, a therapeutic elevation unit may include a first plate coupled to a second plate at a first hinge. A third plate may be coupled to the second plate at a second hinge. At least one inflatable right bladder may be positioned between the first plate and the second plate. At least one inflatable left bladder may be positioned between the second plate and the third plate. The at least one inflatable right bladder may be operable to inflate and deflate to move the second plate to an angle relative to the first plate. The at least one inflatable left bladder may be operable to inflate and deflate to move the third plate to an angle relative to the second plate. Optionally, the first plate, the second plate, and the third plate may be formed from a flexible material.

In some embodiments, the at least one inflatable right bladder may include a right head bladder and a right torso bladder. The right head bladder may be operable to inflate and deflate to move a head section of the second plate to a head angle relative to the first plate. The right torso bladder may be operable to inflate and deflate to move a torso section of the second plate to a torso angle relative to the first plate. The right head bladder may be operable to inflate and deflate to a first capacity. The right torso bladder may be operable to inflate and deflate to a second capacity. The first capacity may be different than the second capacity. The right head bladder and the right torso bladder may cooperate to form a compound angle.

Alternatively, or in addition to, the at least one inflatable left bladder may include a left head bladder and a left torso bladder. The left head bladder may be operable to inflate and deflate to move a head section of the second plate to a head angle relative to the first plate. The left torso bladder may be operable to inflate and deflate to move a torso section of the second plate to a torso angle relative to the first plate. The left head bladder may be operable to inflate and deflate to a first capacity. The left torso bladder may be operable to inflate and deflate to a second capacity. The first capacity may be different than the second capacity. The left head bladder and the left torso bladder may cooperate to form a compound angle.

BRIEF DESCRIPTION OF THE DRAWINGS

The detailed description particularly refers to the accompanying figures in which.

DETAILED DESCRIPTION

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

The embodiments described herein relate to devices, systems and methods to reduce the occurrence and/or duration of or prevent sleep apnea events and/or snoring. The embodiments demonstrate efficacy in preventing mild to moderate obstructive sleep apnea, with improved tolerability relative to current therapy (i.e., CPAP).

The described devices, systems and methods are not limited to the specific embodiments described herein. In addition, components of each device, system and/or steps of each method may be practiced independent and separate from other components and method steps, respectively, described herein. Each component and method also can be used in combination with other systems and methods.

A therapeutic support apparatus 10 provides graduated lateral rotation of a sleep surface 11, along with other positional therapies, e.g. elevated head-of-bed, and techniques to interrupt sleep disordered breathing. Users of analgesic machines that have risk of respiratory depression are at a higher risk of "dead in bed" syndrome. By combining one or more techniques for managing sleep disordered breathing, the therapeutic support apparatus 10 provides interventions to minimize user discomfort (and maximize user adherence to the therapy) while ensuring that the user will be effectively treated in the management of their sleep disorder. The therapeutic support apparatus 10 monitors the user for sleep disordered breathing and activates therapy based on user's sleep environment, immediate or historic efficacy of therapies, and available interventions. In some embodiments, one or more physical interventions may be utilized to manage sleep disordered breathing.

Figure 1:
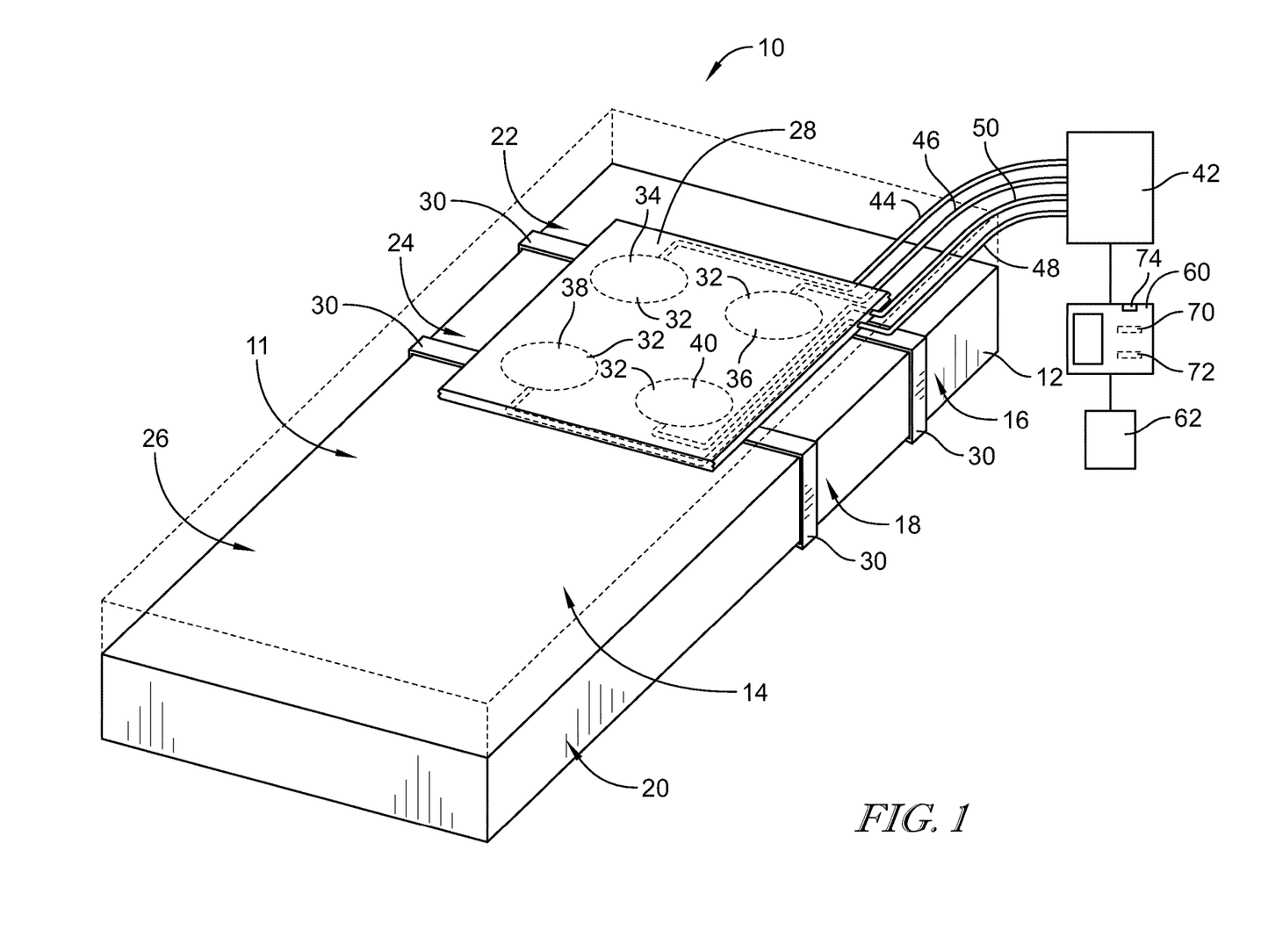
FIG. 1 is a perspective view of a bed frame and mattress (in phantom) according to an illustrative embodiment of the present disclosure, showing an elevation unit embodied as a set of bladders (in phantom) situated between the mattress and the bed frame.

Referring to FIG. 1, therapeutic support apparatus 10 includes a frame 12 and a user support surface 14 positioned on the frame 12. The therapeutic support apparatus 10 may be a hospital bed or a standard bed, e.g. a bed at a user's home or at a care facility. The frame 12 includes a head section 16, a torso section 18 extending from the head section 16, and a foot section 20 extending from the torso section 18. In some embodiments, the frame 12 may include at least one actuator (not shown) to move the head section 16, torso section 18, and foot section 20 relative to one another. For example, the frame 12 may be moveable between a flat position, a Trundelburg position, and/or a head-up position. The user support surface 14 is illustrated as a mattress; however other user support surfaces may be positioned on the frame 12. In an embodiment where the frame 12 is moveable, the user support surface 14 moves with the frame 12. The user support surface 14 includes a head support surface 22 positioned under the head section 16, a torso support surface 24 positioned under the torso section 18, and a foot support surface 26 positioned under the foot section 20, which collectively form the sleep surface 11.

An elevation unit 28 is positioned between the user support surface 14 and the frame 12. In the illustrative embodiment, the elevation unit 28 is positioned under the head support surface 22 and the torso support surface 24. In some embodiments, the elevation unit 28 may also be positioned under the foot support surface 26. The elevation unit 28 is secured to the frame 12 at least one strap 30. The elevation unit 28 includes a plurality of inflatable bladders 32. In the illustrative embodiment, the elevation unit 28 includes a left head bladder 34, a right head bladder 36, a left torso bladder 38, and a right torso bladder 40. In some embodiments, the elevation unit 28 may also include foot bladders (not shown). The bladders 32 are fluidly coupled to an air system 42 that includes a pump to inflate and deflate the bladders 32. Each bladder 34, 36, 38, and 40 is coupled to the air system 42 via a respective hose 44, 46, 48, and 50.

The bladders 32 are operable to inflate and deflate to a desired capacity to angle the user support surface 14. The left head bladder 34 and the right head bladder 36 are operable to inflate and deflate to move the head support surface 22 to a desired head angle. In some embodiments, only one of the left head bladder 34 and the right head bladder 36 is inflated to create the head angle of the head support surface 22. The left torso bladder 38 and the right torso bladder 40 are operable to inflate and deflate to move the torso support surface 24 to a desired torso angle. In some embodiments, only one of the left torso bladder 38 and the right torso bladder 40 is inflated to create the torso angle of the torso support surface 24. The head angle and the torso angle may combine to create a compound angle of the user support surface 14. In the embodiment shown in FIG. 2, the right head bladder 36 is inflated to a greater capacity than the left head bladder 34, and the right torso bladder 40 is inflated to a greater capacity than the left torso bladder 38 to angle a right side 52 of the user support surface 14 higher than a left side 54 of the user support surface 14. In the embodiment shown in FIG. 3, the left head bladder 34 is inflated to a greater capacity than the right head bladder 36, and the left torso bladder 38 is inflated to a greater capacity than the right torso bladder 40 to angle the left side 54 of the user support surface 14 higher than the right side 52 of the user support surface 14. In other embodiments, only the left head bladder 34 and the right head bladder 36 are inflated to create a head angle, while the left torso bladder 38 and the right torso bladder 40 are left entirely deflated so that the torso support surface 24 is flat.

Therapeutic support apparatus 10 also includes a control system 60 and a handheld control pendant 62. Control system 60 is removably attached to a footboard of the frame 12 and handheld control pendant 62 is removably attached to a siderail of the frame 12. The handheld control pendant 62 is illustrated as being coupled to the control system 60 by a wire; however, the handheld control pendant 62 may remotely communication with the control system 60 using infrared, wireless, Bluetooth, or the like. Thus, elevation unit 28, control system 60, and handheld control pendant 62 are all coupled to each other and transferrable to different beds. The control system 60 includes a suitable computer-implemented control system that is operatively coupled to air system 42, such as in operational control communication with air system 42. Air system 42 includes electronics, valves, and one or more compressors necessary to introduce and remove air from the bladders 32 of elevation unit 28. Control system 60 has a user interface 64 to allow a user or caregiver to control elevation unit 28 with air system 42. In some embodiments the control system 60 or handheld control pendant 62 includes a timer that communicates with the air system 42. During a time period in which a user typically takes to fall asleep, the elevation unit 28 is controlled to be in the flat or collapsed positions and thereafter, the components of air system 42 operate to slowly inflate at least one of bladders 32 to preset therapeutic head and/or torso angles over a predetermined span of time. The angle of elevation unit 28 is individually selectable with handheld control pendant 62.

The control system 60 includes one or more processors 70 and one or more sleep monitors 72, such as one or more sensors, coupled in signal communication with processors 70. Sleep monitors 72 are configured to monitor the user's sleep patterns and transmit signals indicative of the sensed sleep patterns to processors 70 for manipulation and evaluation of the data. Based at least in part on the one or more signals received from one or more sleep monitors 72, control system 60 is configured to expand or contract the elevation unit 28 to reposition the user during sleep to prevent or limit the occurrence of a sleep apnea episode, for example.

In certain embodiments as described herein, therapeutic support apparatus 10 is a dynamic support system, rather than a static support system, that is configured to control the configuration of sleep surface 11 based at least in part on data entered into control system 60 and/or sensed by one or more sleep monitors 72, for example, to improve the performance of sleep surface 11 in terms of clinical efficacy and user tolerability.

The therapeutic support apparatus 10 includes, in addition to other components, a plurality of sleep monitors 72 configured to sense and monitor various activities including without limitation, the user's body position, a location of the user with respect to sleep surface 11, an orientation, for example, a left side orientation or a rights side sleep orientation, of the user, the user's vital signs including his/her sleep state, and additional relevant user activity during sleep. Each sleep monitor 72 is in signal communication with processors 70 configured to gather relevant data and generate and transmit to processors 70 signals indicative of the data gathered. Sleep monitors 72 are also configured to receive operation control signals from processors 70.

In some embodiments, the sleep monitor 72 may be a pulse monitor, e.g. an electronic heart monitor, to monitor the user's heart rate. The sleep monitor 72 may be at least one of an electrocardiogram, a photoplethysmogram, or an accelerometer to monitor respiratory rate and/or respiratory amplitude. Alternatively, or in addition to, the electrocardiogram and or an electroencephalograph may monitor the user's sleep state. The sleep monitor 72 may include a scale or positional sensor to determine the user's head angle and/or torso angle. Additionally, cameras and/or bed scales may monitor the user's position while sleeping. In some embodiments, the sleep monitor 72 may also include a microphone to monitor the user's snoring.

Data received from sleep monitors 72 is analyzed and operational control signals are transmitted to elevation unit 28 as well as to other components of therapeutic support apparatus 10, such as to air system 42 to activate air system 42 to provide air to elevation unit 28 and/or remove air from elevation unit 28 to adjust sleep surface 11 based on signals generated by sleep monitors 72 and analyzed by processors 70. In one embodiment, control system 60 includes suitable memory to store data sensed and/or generated by sleep monitors 72.

The therapeutic support apparatus 10 may also include at least one alarm 74 to provide alerts based on data from the sleep monitors 72. The alarm 74 may include an audible alarm positioned near the therapeutic support apparatus 10 to alert the user of the therapeutic support apparatus 10. Alternatively, or in addition to, an audible alarm 74 may be provided remotely from the therapeutic support apparatus 10 to alert a caregiver. In some embodiments, the alarm 74 may include a visual alarm, for example a visual indicator at a nurse's station, an alert on a television at the user's home, etc. The alarm 74 functions to alert either the user of the therapeutic support apparatus 10 and/or the user's caregiver when a sleep disorder is detected by at least one of the sleep monitors 72.

Referring to FIG. 4-8, the elevation unit 28 includes first plate 79 coupled to a second plate 80 at a hinge 81 and a third plate 82 coupled to the second plate 80 at a hinge 83. Although described as plates, the plate 79, 80, 82 may be formed from a flexible semi-rigid material, e.g. plastic. The left head bladder 34 and left torso bladder 38 are positioned between the first plate 79 and the second plate 80. The second plate 80 moves relative to the first plate 79 when at least one of the left head bladder 34 and left torso bladder 38 is inflated. At least one expandable tether 84 may couple the first plate 79 to the second plate 80 to maintain a position of the first plate 79 relative to the second plate 80. The right head bladder 36 and right torso bladder 40 are positioned between the second plate 80 and the third plate 82. The third plate 82 moves relative to the second plate 80 when at least one of the right head bladder 36 and right torso bladder 40 is inflated. At least one expandable tether 85 (shown in FIG. 8) may couple the second plate 80 to the third plate 82 to maintain a position of the third plate 82 relative to the second plate 80.

The bladders 32 are distributed between a left side 90 and a right side 92 of the elevation unit. The left head bladder 34 is positioned adjacent the head end 86 and the left side 90. The right head bladder 36 is positioned adjacent the head end 86 and the right side 92. The left torso bladder 38 is positioned adjacent the torso end 88 and the left side 90. The right torso bladder 40 is positioned adjacent the torso end 88 and the right side 92. An envelope 94 encases the bladders 32 and the plates 79, 80, 82. The envelope 94 is formed from a flexible material and forms a bellows that expands and contracts as the plates 79, 80, 82 move relative to one another.

Sleep monitors 72 in the form of displacement monitors 96 are positioned within the elevation unit 28. In the illustrative embodiment, the monitors 96 are coupled to the third plate 82 to monitor a position of the third plate 82. The monitors 96 may be accelerometers or any other suitable monitor for determining position. A head monitor 98 is positioned between the left head bladder 34 and the right head bladder 36 to monitor a head angle of the elevation unit 28. A torso monitor 100 is positioned between the left torso bladder 38 and the right torso bladder 40 to monitor a torso angle of the elevation unit 28. It should be noted that the monitors 96 may be positioned at other locations to provide data related to the head angle and the torso angle of the elevation unit 28.

Hoses 44, 46, 48, and 50 extend from the elevation unit 28. In the illustrative embodiment, hoses 44, 46, 48, and 50 extend from the elevation unit 28. The hoses 44, 46, 48, and 50 extend so that the hoses 44, 46, 48, and 50 may be extended over a head end of the therapeutic support apparatus 10 without interfering with a user sleeping on the user support surface 14. In other embodiments, the hoses 44, 46, 48, and 50 may extend from any other portion of the elevation unit 28. Hose 44 fluidly couples to left head bladder 34, hose 46 fluidly couples to right head bladder 36, hose 48 fluidly couples to left torso bladder 38, and hose 50 fluidly couples to right torso bladder 40. Each of the hoses 44, 46, 48, and 50 is fluidly coupled to the air system 42 to supply air to left head bladder 34, right head bladder 36, left torso bladder 38, and right torso bladder 40.

Figure 5:
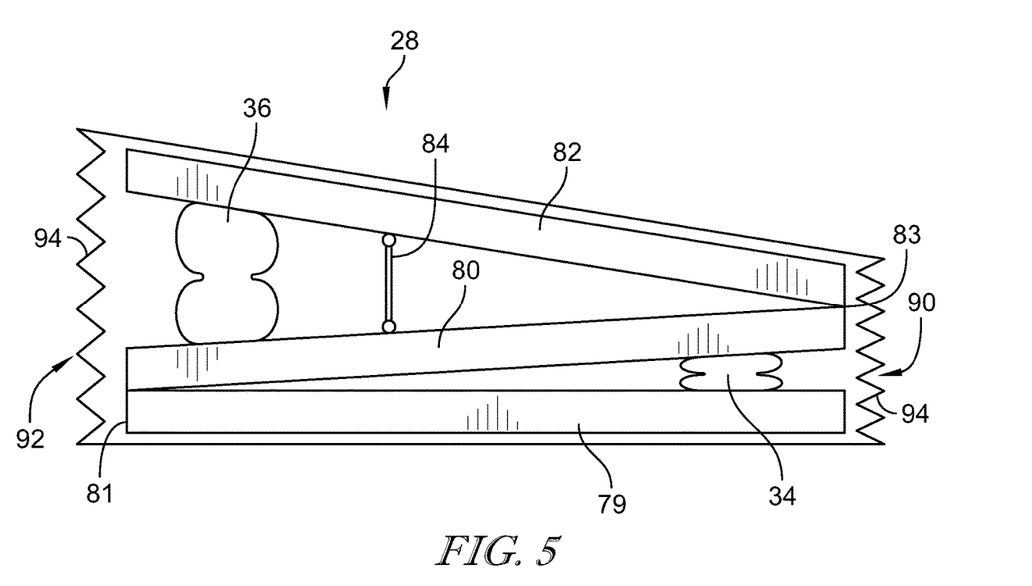
FIG. 5 is an elevation head side view of the elevation unit shown in FIG. 4 having the right side bladders inflated.

FIG. 5 illustrates the elevation unit 28 as viewed from the head end 86. In the embodiment shown in FIG. 5, the head side of the envelope 94 has been removed to illustrate the bladders 32. The right head bladder 36 is inflated to raise the third plate 82 relative to the second plate 80. Notably, the right torso bladder 40 (not shown in FIG. 5) may also be inflated. The third plate 82 is raised from the second plate 80 to form the head angle. In the illustrative embodiment, the left head bladder 34 and the left torso bladder 38 (not shown in FIG. 5) are completely deflated. In other embodiments, the left head bladder 34 and the left torso bladder 38 may be partially inflated to provide additional support to the third plate 82. The tether 85 may facilitate maintaining a position of the third plate 82 relative to the second plate 80. A right side of the envelope 94 is illustrated in FIG. 5. The envelope 94 expands with the elevation unit 28 in a bellows-like manner such that the bladders 32 remain positioned within the envelope 94.

Figure 2:
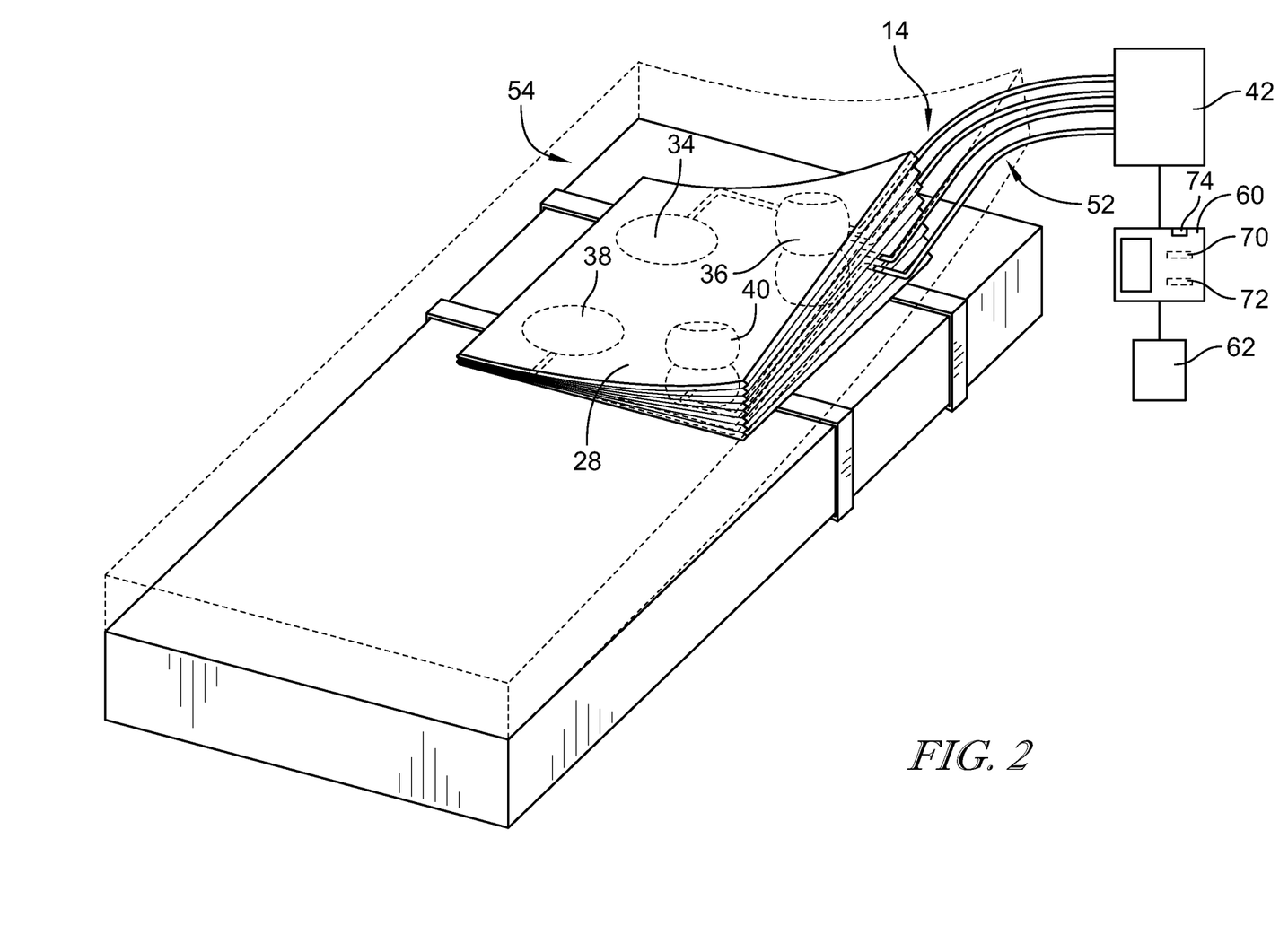
FIG. 2 is a perspective view of the elevation unit of FIG. 1 raising a right side of the mattress to form a compound head/torso angle.
Figure 3:
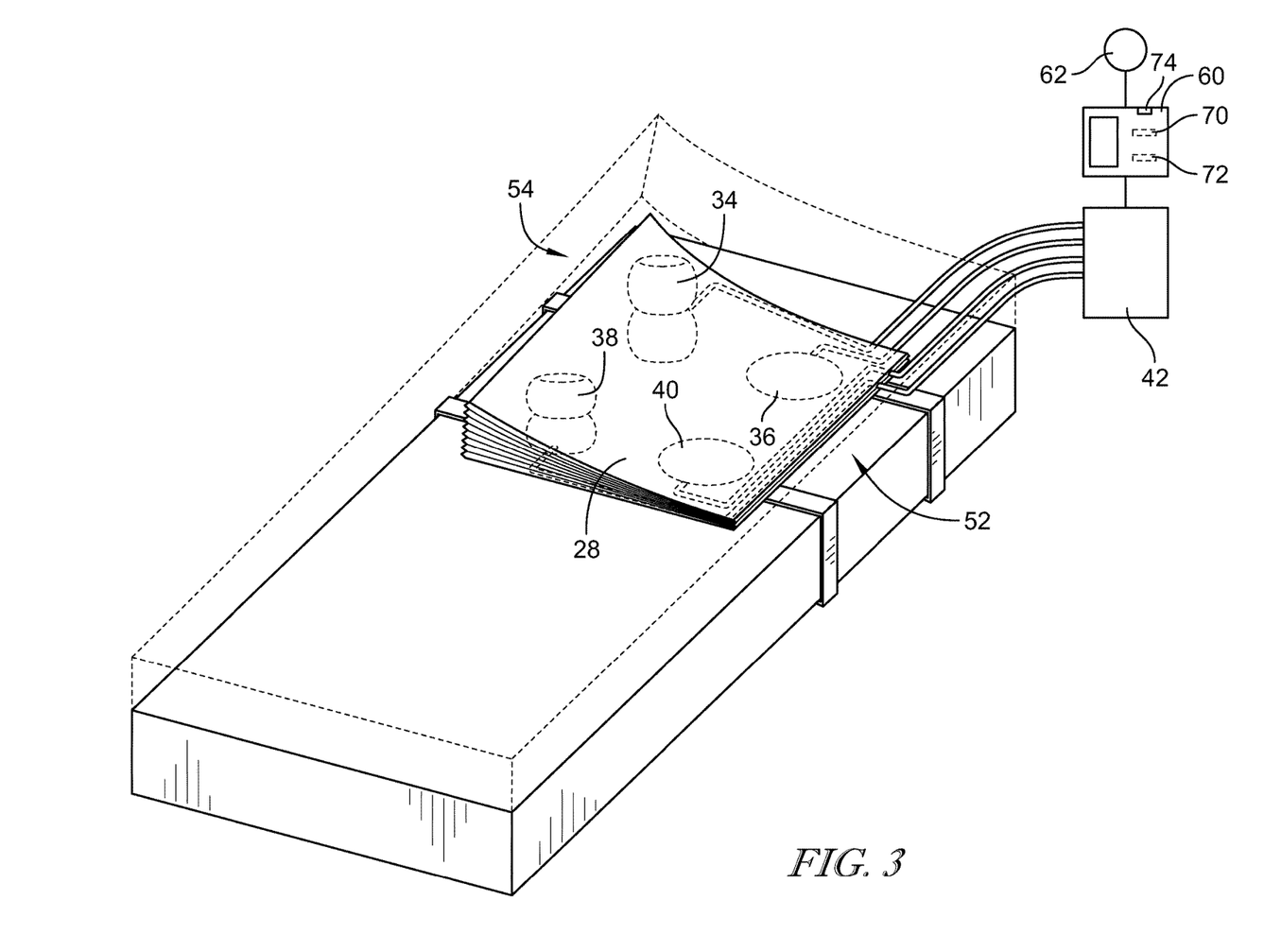
FIG. 3 is a perspective view of the elevation unit similar to FIG. 2 raising a left side of the mattress to form a compound head/torso angle.
Figure 4:
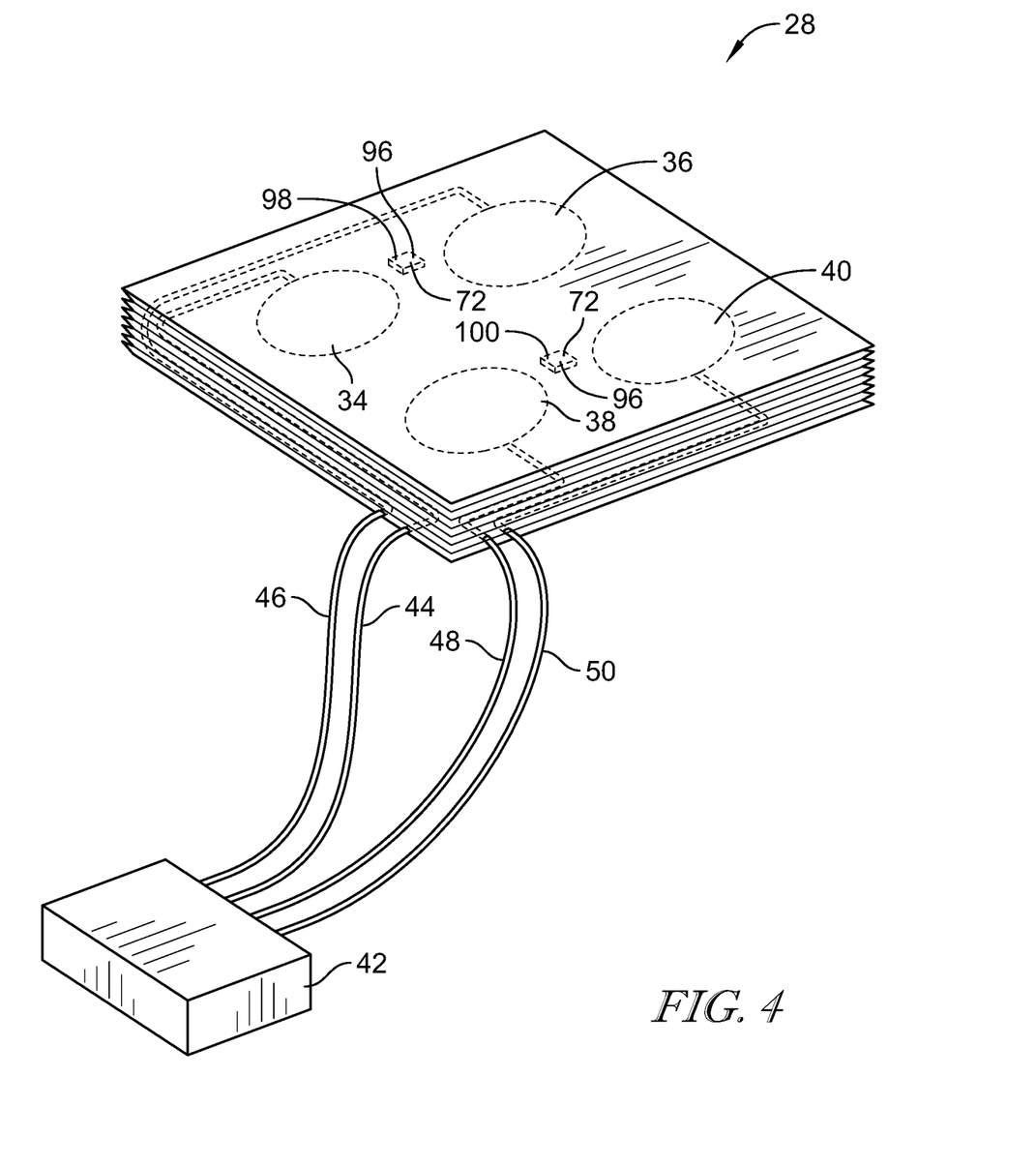
FIG. 4 is a perspective view of the elevation unit shown in FIG. 1 coupled to a source of air.
Figure 6:
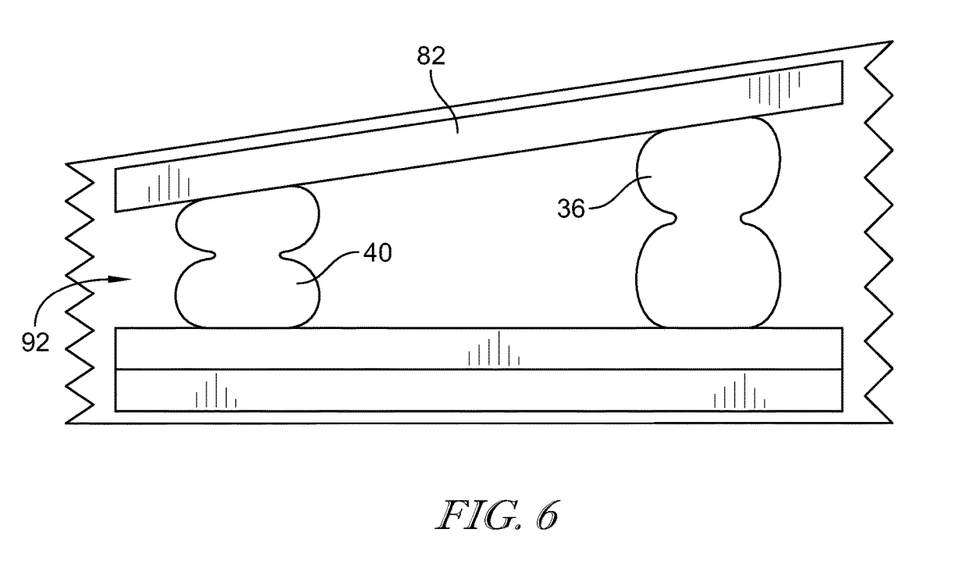
FIG. 6 is an elevation right side view of the elevation unit shown in FIG. 4 having the right head bladder inflated to a greater capacity than the right torso bladder.
Figure 7:
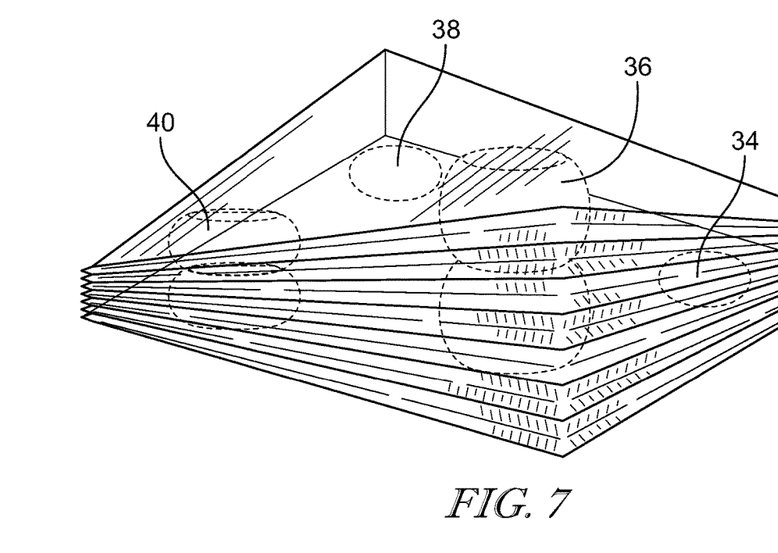
FIG. 7 is a perspective view of the elevation unit shown in FIG. 4 having the right head bladder inflated to a greater capacity than the right torso bladder.
Figure 8:
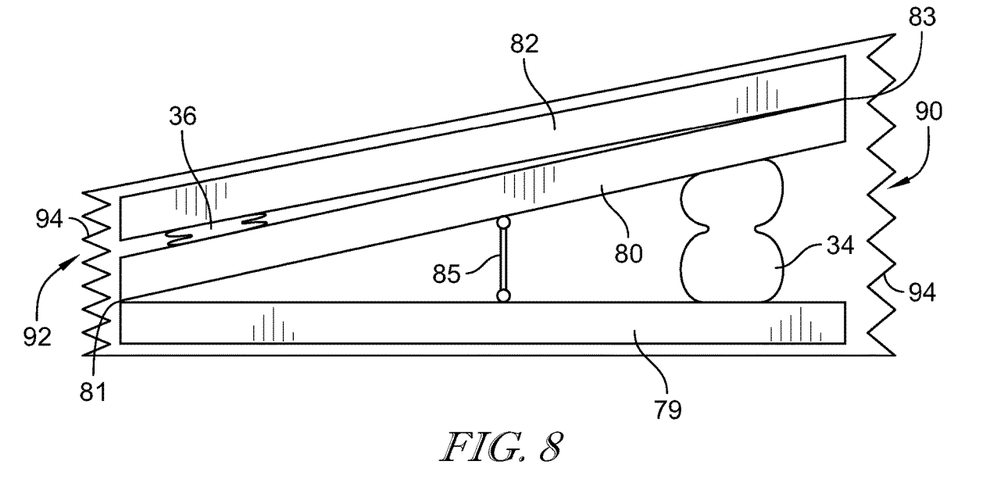
FIG. 8 is an elevation head side view of the elevation unit shown in FIG. 4 having the left side bladders inflated.

Referring to FIG. 6, the elevation unit 28 is illustrated from the right side 92. The right head bladder 36 is inflated to a first capacity. The right torso bladder 40 is inflated to a second capacity that is less than the first capacity. By inflating the right head bladder 36 to a greater capacity than the right torso bladder 40, while deflating the left head bladder 34 and the left torso bladder 38, the third plate 82 forms a compound angle defined by the head angle and a torso angle, as illustrated in FIG. 7. Again, it should be noted that the left head bladder 34 and the left torso bladder 38 may also be inflated for additional support. In such an embodiment, the left head bladder 34 is inflated to a lesser capacity than the right head bladder 36, and the left torso bladder 38 is inflated to a lesser capacity than the right torso bladder 40. The embodiments illustrated in FIGS. 4-7 show the right side 92 of the elevation unit 28 inflated to raise the right side 52 of the user support surface 14 higher than the left side 54 of the user support surface 14, as illustrated in FIG. 2. In the embodiment shown in FIG. 8, the elevation unit 28 is inflated to raise the left side 54 of the user support surface 14 higher than the right side 52 of the user support surface 14, as illustrated in FIG. 3, i.e. the second plate 80 is raised relative to the first plate 79. The head angle and torso angle of the elevation unit 28 may be predetermined to address the user's sleep apnea and reduce oxygen desaturation during sleep.

Figure 9:
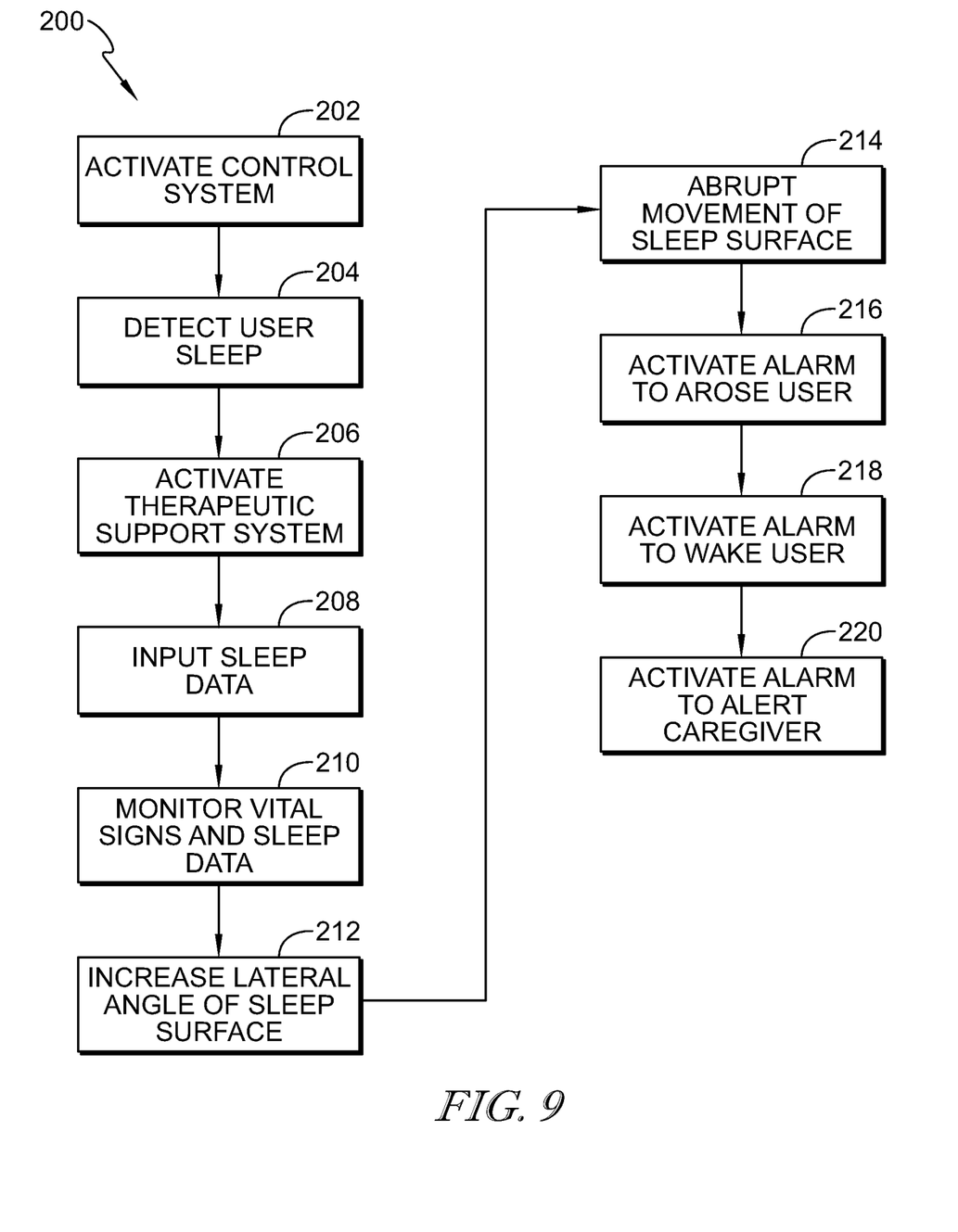
FIG. 9 is a flowchart illustrating a method for operating the elevation unit shown in FIG. 1.

An exemplary method 200 utilizing control system 60 for monitoring the sleep activities of a user positioned on therapeutic support apparatus 10 is illustrated in FIG. 9. The method 200 also includes steps for controlling the user's sleep apnea and reducing oxygen desaturation. As described above, control system 60 includes one or more processors 70 configured to perform the steps as described herein.

Control system 60 is activated 202 to position the user at angles to reduce apnea episodes. For example, the angles may be selected to facilitate preventing oxygen desaturation. The head section 16 may be positioned at a predetermined head angle and the torso section 18 may be positioned at a predetermined torso angle. The sections 16 and 18 may be angled manually by the user or a caregiver. For example, when the user wants to go to sleep, the sections 16 and 18 are manually angled for a desired sleep position. Alternatively, the sections 16 and 18 may automatically angle to the desired sleep position when user sleep is detected by the control system 60. In one embodiment, control system 60 detects 204 when the user begins to fall asleep and activates 206 therapeutic support apparatus 10 on a delay to rotate the user at a suitable time after sleep is detected, such as after the user has been asleep for 30 minutes. In an alternative embodiment, control system 60 is programmed to activate therapeutic support apparatus 10 at a preset time, for example, at a 30 minute delay, without relying on monitoring the user's sleep activity. In a particular embodiment, control system 60 delays inter-sleep rotation of the user until the user is in a deep sleep. Further, when control system 60 detects that the user is waking, control system 60 will activate therapeutic support apparatus 10 to move mattress 14 to an initial configuration such that the user can exit from mattress 14. In a further embodiment, control system 60 prevents activation of therapeutic support apparatus 10 if control system 60 detects the user is sleeping in a lateral decubitus position.

Prior to sleep, the user is able to input 208 to control system 60 sleep data including without limitation, preferred sleeping sides and positions, the user's measurements including, for example, the user's height, weight, and inseam and torso measurements, preferred lateral rotational angles and/or longitudinal rotational angles of one or more support planes defining the sleep surface 11. Based at least in part on the user's input data, control system 60 is configured to activate therapeutic support apparatus 10 to adjust a direction and/or a level of rotation of one or more support planes defining the sleep surface 11. For example, if the user prefers a left side slope to sleep surface 11, control system 60 activates elevation unit 28 to form the desired lateral left side slope, or if the user's partner is sleeping on the left side of the user, a left angle may be created. In one embodiment, minimal adjustments are made to sleep surface 11 to maintain the user's apnea-hypopnea index under 5 and/or prevent snoring because apnea events and snoring may or may not be equivalent, depending on the user.

During sleep, control system 60 actively monitors 210 the user's vital signs and other relevant sleep data. Control system 60 is configured to collect and record data obtained as the user sleeps to diagnose any undesirable or abnormal sleep activities or conditions, including the user's apnea-hypopnea index, for example. The vital signs monitored may include respiratory rate, respiratory amplitude, heart rate, and/or oxygen saturation ($SpO_2$). In some embodiments, the control system 60 may be configured to monitor other user vital signs. Other relevant sleep data may include measurements of the user's head angle and torso angle, the user's apnea-hypopnea index, the user's sleep state, and/or snoring. In some embodiments, other relevant sleep data may be monitored. If the control system 60 monitors adverse sleep data, e.g. abnormally high or low heart rate, abnormally high or low respiratory rate, apnea-hypopnea index above 5, etc., the control system 60 automatically responds to the adverse sleep data to prevent oxygen desaturation. If the user is sensed to be suffering from sleep disordered breathing based on sensed apnea, sensed irregular breathing patter, breath interruption, sound of snoring, $O_2$ desaturation, inadequate head rotation or the like the control 150 may automatically increase 212 a lateral angle of at least one of the head section 16 and the torso section 18 by operating the elevation unit 28 while preserving the user's sleep state. For example, if the head angle of the head section 16 is at 17.5 degrees and the torso angle of the torso section 18 is at 12.5 degrees torso, the angles may be insufficient to manage the user's sleep apnea. Accordingly, at least one of the head angle and the torso angle are slowly increased. For example, the head angle may be increased to 20 degrees and/or the torso angle may be increased to 15 degrees. The control system 60 gradually increases the head angle and the torso angle such that the user's sleep state is uninterrupted.

If altering the lateral angles of the sleep surface 11 fails to improve the user's condition, the lateral angle of at least one of the head section 16 and the torso section 18 may be increased or decreased abruptly 214 to arouse user from the user's current sleep stage, up to and including waking the user. Alternatively, or in addition to, the bead frame 12 or mattress 14 may be vibrated to arouse the user. In some embodiments, the head of the bed frame may be raised to arouse the user. Disturbing the user's sleep may change the user's sleep state, e.g. waking them from sleep stage 3 to sleep stage 1, or all the way to awake. Changes in the user's sleep state (not necessarily awakening the user) may be sufficient to trigger a sympathetic/arousal response that will make the user breath normally. As sleep disordered breathing may be a function of sleep stage, sleep disordered breathing suffered in sleep stage 3 or sleep stage 4 may be resolved if and when user enters sleep stage 1, sleep stage 2, or REM sleep.

If altering the user's sleep state fails to improve the user's condition, the control system 60 may activate 216 alarm 74. Initially, the control system 60 activates a local alarm 74 that is proximate to the therapeutic support apparatus 10 and the user. Activating the local alarm 74 may arouse the user and alter a sleep state of the user as described above. Alternatively, activating 218 the local alarm 74 may entirely wake the user. If the local alarm 74 fails to arouse or wake the user, the control system 60 may activate 220 other remote alarms to notify a caregiver of the adverse sleep condition of the user. The caregiver may then arouse or wake the user to control the adverse sleep condition.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless cannot be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles can have been presented, they need not be utilized in combination, and many combinations of aspects and principles are possible in light of the various embodiments provided above.

The invention claimed is:

1. A therapeutic support apparatus comprising:
a user support surface extending along a longitudinal axis, the user support surface having a head section and a torso section, each of the head section and the torso section being operable to angle relative to the longitudinal axis,
an elevation unit operable to position at least one of the head section and torso section at angles relative to the longitudinal axis,
a monitor to acquire data related to a user while sleeping on the user support surface, and
an alarm operable to activate based on the data acquired by the monitor,
wherein at least one of the elevation unit and the alarm is activated in response to the data acquired by the monitor to control oxygen desaturation of the user,
wherein the elevation unit includes:
a first plate coupled to a second plate at a hinge, and
at least one inflatable bladder positioned between the first plate and the second plate,
wherein the at least one inflatable bladder is operable to inflate and deflate to move the second plate to an angle relative to the first plate,
wherein the at least one inflatable bladder includes a head bladder and a torso bladder,
wherein the head bladder is operable to inflate and deflate to move a head section of the second plate to a head angle relative to the first plate, and
wherein the torso bladder is operable to inflate and deflate to move a torso section of the second plate to a torso angle relative to the first plate.

2. The therapeutic support apparatus of claim 1, wherein:
the head bladder is operable to inflate and deflate to a first capacity, and the torso bladder is operable to inflate and deflate to a second capacity, wherein the first capacity is different than the second capacity,
the head bladder and the torso bladder cooperate to form a compound angle.

3. The therapeutic support apparatus of claim 1, wherein the head angle and the torso angle are different.

4. The therapeutic support apparatus of claim 1, wherein the head angle is greater than the torso angle.

5. The therapeutic support apparatus of claim 4, wherein the head section of the second plate and the torso section of the second plate cooperate to form a compound angle.

6. The therapeutic support apparatus of claim 1, wherein the elevation unit changes a head angle of the head section of the second plate in response to the data acquired by the monitor.

7. The therapeutic support apparatus of claim 1, wherein the elevation unit changes the torso angle of the torso section of the second plate in response to the data acquired by the monitor.

8. The therapeutic support apparatus of claim 1, wherein the elevation unit moves the head section of the second plate in response to the data acquired by the monitor to alter a sleep stage of the user.

9. The therapeutic support apparatus of claim 1, wherein the elevation unit moves the torso section of the second plate in response to the data acquired by the monitor to alter a sleep stage of the user.

10. The therapeutic support apparatus of claim 1, further comprising at least one tether coupling the first plate and the second plate.

11. The therapeutic support apparatus of claim 1, wherein the elevation unit includes an expandable envelope, wherein the first plate, the second plate, and the at least one inflatable bladder are housed within the expandable envelope.

12. The therapeutic support apparatus of claim 1, wherein the elevation unit includes:
a third plate coupled to the second plate at a second hinge,
at least one inflatable right bladder positioned between the first plate and the second plate, and at least one inflatable left bladder positioned between the second plate and the third plate,
wherein the at least one inflatable right bladder is operable to inflate and deflate to move the second plate to an angle relative to the first plate, and
wherein the at least one inflatable left bladder is operable to inflate and deflate to move the third plate to an angle relative to the second plate.

13. The therapeutic support apparatus of claim 12, wherein the first plate, the second plate, and the third plate are formed from a flexible material.

14. The therapeutic support apparatus of claim 12, wherein the at least one inflatable right bladder includes a right head bladder and a right torso bladder,
wherein the right head bladder is operable to inflate and deflate to move a head section of the second plate to a head angle relative to the first plate, and
wherein the right torso bladder is operable to inflate and deflate to move a torso section of the second plate to a torso angle relative to the first plate.

15. The therapeutic support apparatus of claim 14, wherein:
the right head bladder is operable to inflate and deflate to a first capacity, and the right torso bladder is operable to inflate and deflate to a second capacity, wherein the first capacity is different than the second capacity,
the right head bladder and the right torso bladder cooperate to form a compound angle.

16. The therapeutic support apparatus of claim 12, wherein the at least one inflatable left bladder includes a left head bladder and a left torso bladder,
wherein the left head bladder is operable to inflate and deflate to move a head section of the second plate to a head angle relative to the first plate, and
wherein the left torso bladder is operable to inflate and deflate to move a torso section of the second plate to a torso angle relative to the first plate.

17. The therapeutic support apparatus of claim 16, wherein:
the left head bladder is operable to inflate and deflate to a first capacity, and the left torso bladder is operable to inflate and deflate to a second capacity, wherein the first capacity is different than the second capacity,
the left head bladder and the left torso bladder cooperate to form a compound angle.

18. The therapeutic support apparatus of claim 1, wherein the user support surface is positioned on a frame, wherein the elevation unit is positioned between the frame and the user support surface.

19. The therapeutic support apparatus of claim 18, wherein the elevation unit includes at least one strap to secure the elevation unit to the frame.

20. The therapeutic support apparatus of claim 1, wherein the alarm is an audible alarm.

21. The therapeutic support apparatus of claim 1, wherein the alarm is a visual alarm.

22. The therapeutic support apparatus of claim 1, wherein the data acquired includes at least one of head angle and torso angle.

23. The therapeutic support apparatus of claim 1, wherein the data acquired includes at least one of respiratory rate, respiratory amplitude, oxygen saturation, apnea hypopnea index, sleep state, and snoring.

24. A therapeutic support apparatus comprising:
a user support surface extending along a longitudinal axis, the user support surface having a head section and a torso section, each of the head section and the torso section being operable to angle relative to the longitudinal axis,
an elevation unit operable to position at least one of the head section and torso section at angles relative to the longitudinal axis,
a monitor to acquire data related to a user while sleeping on the user support surface, and
an alarm operable to activate based on the data acquired by the monitor,
wherein at least one of the elevation unit and the alarm is activated in response to the data acquired by the monitor to control oxygen desaturation of the user,
wherein the elevation unit includes:
a first plate coupled to a second plate at a first hinge,
a third plate coupled to the second plate at a second hinge,
at least one inflatable right bladder positioned between the first plate and the second plate, and
at least one inflatable left bladder positioned between the second plate and the third plate,
wherein the at least one inflatable right bladder is operable to inflate and deflate to move the second plate to an angle relative to the first plate,
wherein the at least one inflatable left bladder is operable to inflate and deflate to move the third plate to an angle relative to the second plate,
wherein the at least one inflatable right bladder includes a right head bladder and a right torso bladder,
wherein the right head bladder is operable to inflate and deflate to move a head section of the second plate to a head angle relative to the first plate, and
wherein the right torso bladder is operable to inflate and deflate to move a torso section of the second plate to a torso angle relative to the first plate.

25. A therapeutic support apparatus comprising:
a user support surface extending along a longitudinal axis, the user support surface having a head section and a torso section, each of the head section and the torso section being operable to angle relative to the longitudinal axis,
an elevation unit operable to position at least one of the head section and torso section at angles relative to the longitudinal axis,
a monitor to acquire data related to a user while sleeping on the user support surface, and
an alarm operable to activate based on the data acquired by the monitor,
wherein at least one of the elevation unit and the alarm is activated in response to the data acquired by the monitor to control oxygen desaturation of the user,
wherein the elevation unit includes:
a first plate coupled to a second plate at a first hinge,
a third plate coupled to the second plate at a second hinge,
at least one inflatable right bladder positioned between the first plate and the second plate, and
at least one inflatable left bladder positioned between the second plate and the third plate,
wherein the at least one inflatable right bladder is operable to inflate and deflate to move the second plate to an angle relative to the first plate,
wherein the at least one inflatable left bladder is operable to inflate and deflate to move the third plate to an angle relative to the second plate,
wherein the right head bladder is operable to inflate and deflate to a first capacity, and the right torso bladder is operable to inflate and deflate to a second capacity, wherein the first capacity is different than the second capacity, and wherein the right head bladder and the right torso bladder cooperate to form a compound angle.

26. A therapeutic support apparatus comprising:

a user support surface extending along a longitudinal axis, the user support surface having a head section and a torso section, each of the head section and the torso section being operable to angle relative to the longitudinal axis, an elevation unit operable to position at least one of the head section and torso section at angles relative to the longitudinal axis, a monitor to acquire data related to a user while sleeping on the user support surface, and an alarm operable to activate based on the data acquired by the monitor, wherein at least one of the elevation unit and the alarm is activated in response to the data acquired by the monitor to control oxygen desaturation of the user, wherein the elevation unit includes:

a first plate coupled to a second plate at a first hinge, a third plate coupled to the second plate at a second hinge, at least one inflatable right bladder positioned between the first plate and the second plate, and at least one inflatable left bladder positioned between the second plate and the third plate, wherein the at least one inflatable right bladder is operable to inflate and deflate to move the second plate to an angle relative to the first plate, wherein the at least one inflatable left bladder is operable to inflate and deflate to move the third plate to an angle relative to the second plate, wherein the at least one inflatable left bladder includes a left head bladder and a left torso bladder, wherein the left head bladder is operable to inflate and deflate to move a head section of the second plate to a head angle relative to the first plate, and wherein the left torso bladder is operable to inflate and deflate to move a torso section of the second plate to a torso angle relative to the first plate.

* * * * *